(12) United States Patent
Seeram et al.

(10) Patent No.: US 8,183,282 B2
(45) Date of Patent: May 22, 2012

(54) THERAPEUTIC USES OF UROLITHINS

(75) Inventors: Navindra P. Seeram, Los Angeles, CA (US); David Heber, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 609 days.

(21) Appl. No.: 12/298,122

(22) PCT Filed: Apr. 26, 2007

(86) PCT No.: PCT/US2007/010054
§ 371 (c)(1),
(2), (4) Date: Jan. 28, 2009

(87) PCT Pub. No.: WO2007/127263
PCT Pub. Date: Nov. 8, 2007

(65) Prior Publication Data
US 2009/0326057 A1    Dec. 31, 2009

Related U.S. Application Data

(60) Provisional application No. 60/745,717, filed on Apr. 26, 2006.

(51) Int. Cl.
*A61K 31/366* (2006.01)
(52) U.S. Cl. ........................................ 514/455
(58) Field of Classification Search .................. None
See application file for complete search history.

(56) References Cited

U.S. PATENT DOCUMENTS
7,678,549 B2 * 3/2010 Buxton .................. 435/7.23

OTHER PUBLICATIONS

Adams; et al., "Pomegranate Juice, Total Pomegranate Ellagitannins, and Punicalagin Suppress Inflammatory Cell Signalling in Colon Cancer Cells", J. Agric. Food Chem. (2006), 54:980-985.
Afaq; et al., "Anthocyanin- and Hydrolyzable Tannin-Rich Pomegranate Fruit Extract Modulates MAPK and NF-KappaB Pathways and Inhibits Skin Tumorigenesis in CD-1 Mice", Int. J. Cancer (2005), 113:423-433.
Afaq; et al., "Pomegranate Fruit Extract Modulates UV-B-mediated Phosphorylation of Mitogen-activated Protein Kinases and Activation of Nuclear Factor Kappa B in Normal Human Epidermal Keratinocytes", Photochemistry and Photobiology (2005), 81:38-45.
Albrecht; et al., "Pomegranate Extracts Potently Suppress Proliferation, Xenograft Growth, and Invasion of Human Prostate Cancer Cells", Journal of Medicinal Food (2004), 7(3):274-283.
Cerda; et al., "Evaluation of the bioavailability and metabolism in the rat of punicalagin, an antioxidant polyphenol from pomegranate juice", Eur. J. Nutr. (2003), 42:18-28.
Cerda; et al., "Metabolism of Antioxidant and Chemopreventive Ellagitannins from Strawberries, Rasberries, Walnuts, and Oak-Aged Wine in Humans: Identification of Biomarkers and Individual Variability", J. Agric. Food Chem. (2005), 53:227-235.
Cerda; et al., "Pomegranate juice supplementation in chronic obstructive pulmonary disease: a 5-week randomized, double-blind, placebo-controlled trial", European Journal of Clinical Nutrition (2006): 60:245-253.
Cerda; et al., "Repeated Oral Administration of High Doses of the Pomegranate Ellagitannin Punicalagin to Rats for 37 Days Is Not Toxic", J. Agric. Food Chem. (2003), 51:3493-3501.
Cerda; et al., "The potent in vitro antioxidant ellagitannins from pomegranate juice are metabolised into bioavailable but poor antioxidant hydroxy-6H-dibenzopyran-6-one derivatives by the colonic microflora of healthy humans", Eur. J. Nutr. (2004), 43:205-220.
Lansky; et al., "Possible synergistic prostate cancer suppression by anatomically discrete pomegranate fractions", Investigational New Drugs (2005), 23:11-20.
Larrosa; et al., "Urolithins, Ellagic Acid-Derived Metabolites Produced by Human Colonic Microflora, Exhibit Estrogenic and Antiestrogenic Activities", J. Agric. Food Chem. (2006), 54:1611-1620.
Malik; et al., "Pomegranate fruit juice for chemoprevention and chemotherapy of prostate cancer", PNAS (2005), 102(41):14813-8.
Seeram; et al., "In vitro antiproliferative, apoptotic and antioxidant activies of punicalagin, ellagic acid and a total pomegranate tannin extract are enhanced in combination with other polyphenols as found in pomegranate juice", Journal of Nutritional Biochemistry (2005), 16:360-367.
Seeram; et al., "Pomegranate Juice Ellagitannin Metabolites Are Present in Human Plasma and Some Persist in Urine for Up to 48 Hours", The Journal of Nutrition (2006), 136:2481-2485.
Kiss; et al., "Induction of neutral endopeptidase activity in PC-3 cells by an aqueous extract of Epilobium angustifolium L. and oenothein B", Phytomedicine (2006), 13(4):284-289.
Sakagami H; et al., "Cytotoxic activity of hydrolyzable tannins against human oral tumor cell lines: A possible mechanism", Phytomedicine (2000), 7(1):39-47, abstract only.

* cited by examiner

*Primary Examiner* — James D Anderson
(74) *Attorney, Agent, or Firm* — Bozicevic, Field & Francis LLP; Pamela J. Sherwood

(57) ABSTRACT

The subject invention is drawn to ellagitannin metabolites (e.g., urolithin) that find use in treating or preventing a neoplastic disease in a subject.

16 Claims, 7 Drawing Sheets

A

B

THERAPEUTIC USES OF UROLITHINS

FEDERALLY SPONSORED RESEARCH AND DEVELOPMENT

This invention was made with Government support of Grant No. AT000151 awarded by the National Institutes of Health. The Government has certain rights in this invention.

INTRODUCTION

Ellagitannins (ETs) are polymeric polyphenols abundant in some fruits and nuts such as pomegranates, raspberries, strawberries, black raspberries, walnuts and almonds. Despite numerous reports of the biological properties and human health benefits of ETs, knowledge of their bioavailability, pharmacokinetics, disposition and metabolic fate in humans is limited. Pomegranate (*Punica granatum* L.) fruits are widely consumed fresh and as beverages such as juice (PJ). In commercial juice processing methods, ETs which are abundant in the fruit peels, are extracted in large quantities into the juice. Punicalagin [2,3 hexahydroxydiphenoyl-4,6-gallagylglucose], which occurs as isomers (FIG. 1), is the predominant ET present in PJ as a result of this process. ETs belong to the chemical class of hydrolyzable tannins, which release ellagic acid (EA) on hydrolysis. In addition, PJ contains other polyphenols such as anthocyanins, which are present in the fruit arils, imparting its brilliant ruby-red color.

The potent antioxidant properties of PJ have been attributed to its high content of punicalagin isomers which can reach levels >2 g/L juice. ETs have also been identified as the active anti-atherogenic compounds in PJ. It has been suggested that pomegranate ETs and pomegranate fruit extracts inhibit the proliferation of human cancer cells and modulate inflammatory sub-cellular signaling pathways and apoptosis, see, for example, Seeram et al. (2005) J Nutr Biochem. 2005; 16:360-7; Adams et al. (2006) J Agric Food Chem. 2006, 54, 980-85; Afaq et al. (2005) Photochem Photobiol. 2005; 81:38-45; Afaq et al. (2005) Int J Cancer. 2005;113:423-33. Pomegranate fruit extract has also been suggested to reduce prostate tumor growth and prostate serum antigen (PSA) levels in athymic nude mice implanted with CWR22Rv1 prostate cells (Malik et al. (2005) Proc Natl Acad Sci. 2005; 102: 14813-8.

Although the absorption, metabolism, distribution and excretion of pomegranate ETs in animals and in humans, have been reported, their pharmacokinetic parameters remain uninvestigated. It is becoming clear that considerable inter-individual variability occurs in polyphenol metabolism in humans. As such, there is a need to establish bioavailability, metabolism and pharmacokinetic parameters of pomegranate ETs in human volunteers and to link ETs and/or metabolites thereof to specific beneficial properties, e.g., antioxidant, cancer cell antiproliferative and pro-apoptotic effects, etc. This invention meets these and other needs.

SUMMARY OF THE INVENTION

The present invention is drawn to metabolites of pomegranate polyphenols (e.g., ellagitannins) or derivatives thereof, which polyphenols find use in methods of treating and/or preventing a hyperproliferative disease in a subject. The subject ellagitannin metabolites are shown herein to have an anti-proliferative and/or pro-apoptotic effect on cells, and as such, find use in the treatment and prevention of a number of disease states, e.g. to inhibit tumor growth, to decrease inflammation associated with a lymphoproliferative disorder, to inhibit graft rejection, or neurological damage due to tissue repair, etc.

In one embodiment of the invention, a pharmaceutical composition is provided, comprising an effective dose of an ellagitannin metabolite and a pharmaceutically acceptable excipient. The effective dose will usually be effective for inhibiting the proliferation of a cell, including tumor cells, e.g. solid tumor cells, such as carcinomas, e.g. pancreatic carcinomas, prostate carcinomas, and the like. In certain embodiments, the ellagitannin metabolites of interest are urolithins and/or derivatives thereof.

In another embodiment of the invention, methods are provided for inhibiting undesirable cell proliferation, the method comprising contacting the cells with an effective dose of an ellagitannin metabolite and a pharmaceutically acceptable excipient. Cells of interest include, without limitation, tumor cells, e.g. solid tumor cells, such as carcinomas, e.g. pancreatic carcinomas, prostate carcinomas, and the like. In certain embodiments, the ellagitannin metabolites of interest are urolithins and/or derivatives thereof.

In some embodiments of the invention, patients are classified as metabolite producers and metabolite non-producers, where treatment may be tailored to the status of the patient.

DESCRIPTION OF THE SPECIFIC EMBODIMENTS

Figure 1:
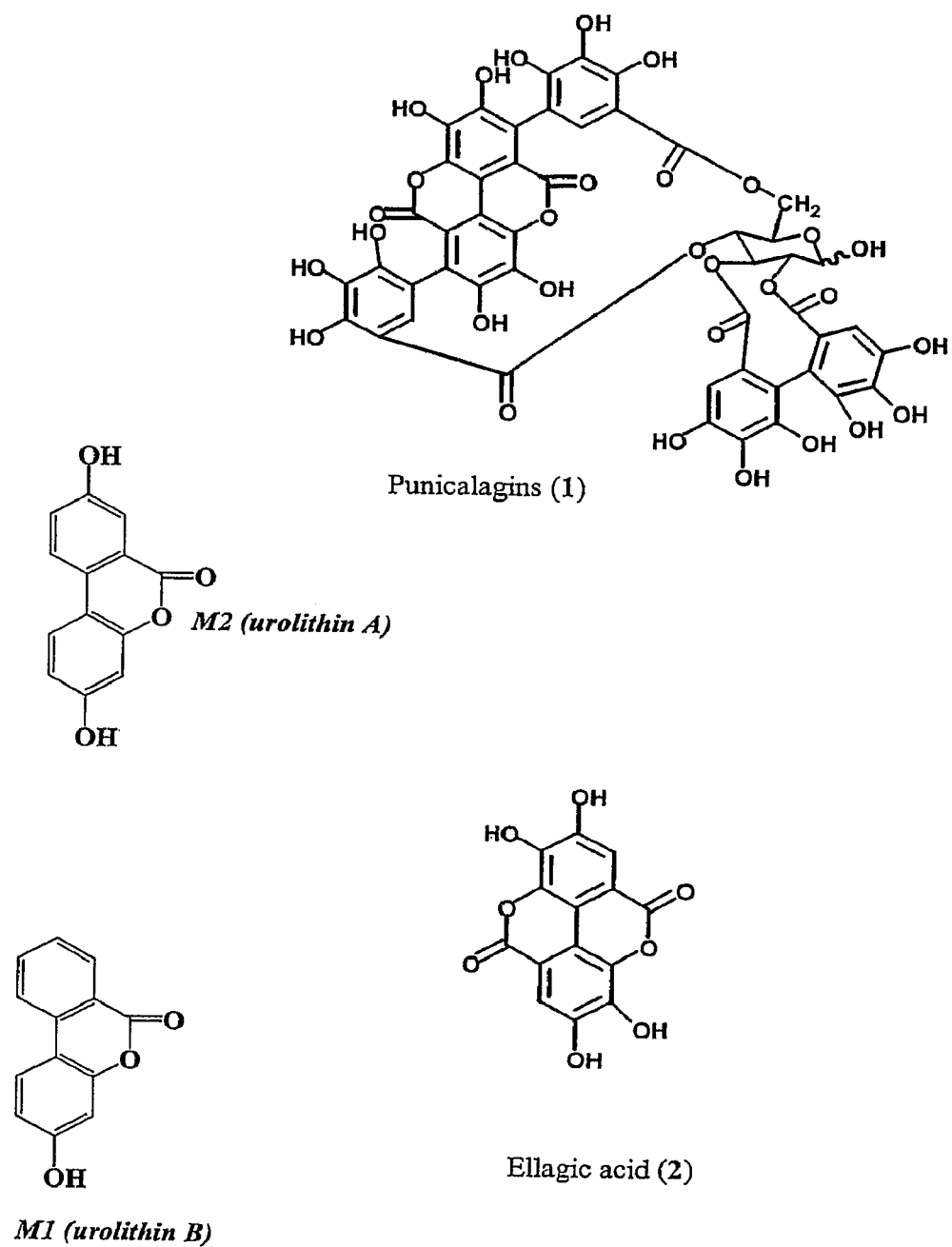
FIG. 1: Chemical structures of punicalagin isomers (1), the major ellagitannin (ET) present in pomegranate juice, and its hydrolysis product, ellagic acid (EA) (2).
Figure 2:
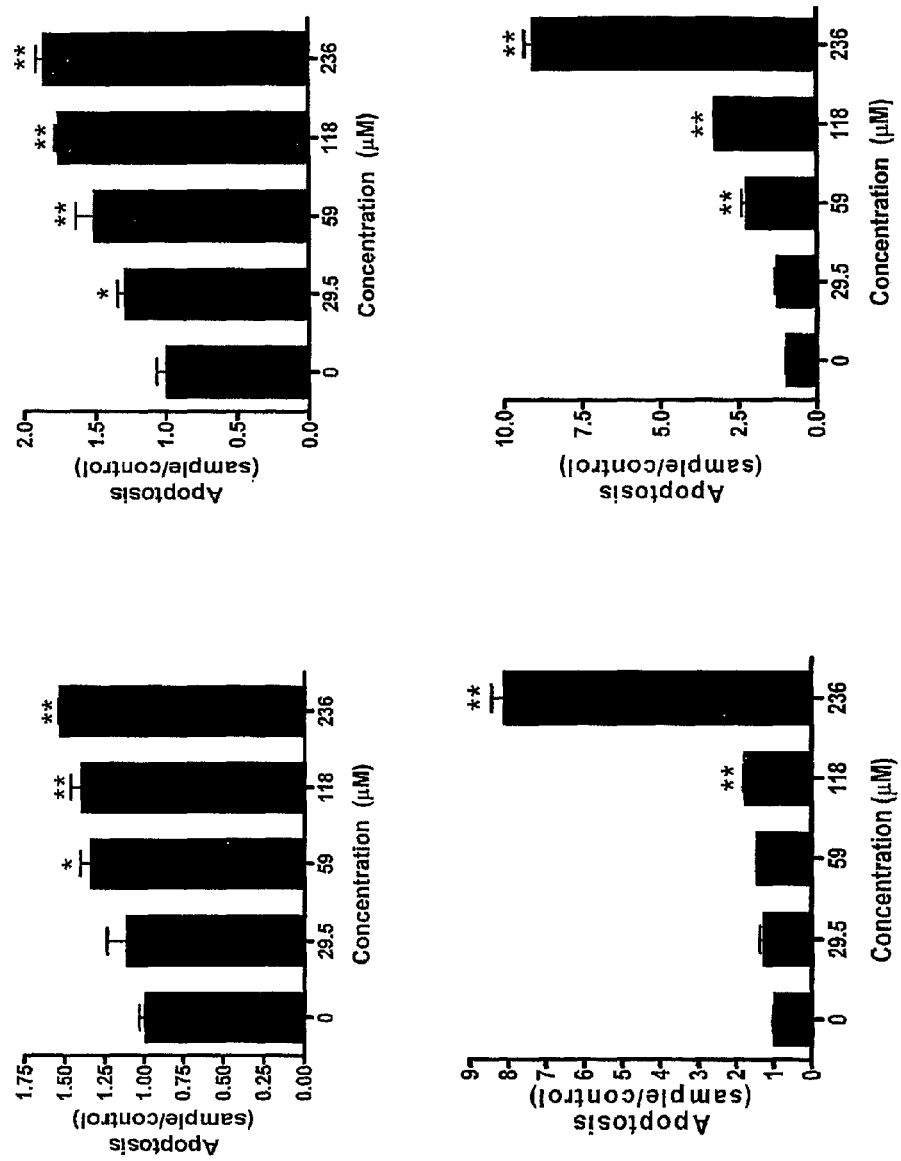
FIG. 2: Pro-apototic activity of urolithin B against four human prostate cancer cell lines: A=22Rv1; B=PC3; C=LNCaP; D=LNCaP-AR. Statistical significance are: *p=0.05 and **p=0.01.

The present invention is drawn to metabolites of pomegranate polyphenols (e.g., ellagitannins) that find use in methods of treating and/or preventing a neoplastic disease in a subject. The subject ellagitannin metabolites are shown herein to have an anti-proliferative and/or pro-apoptotic effect, and as such, find use in the treatment and prevention of a number of hyperproliferative disease states. Among the tumor cells found to be sensitive to treatment with elagitannin metabolites are solid tumors, e.g. carcinomas such as pancreatic carcinoma cells, colon carcinoma cells, etc. Treatment of prostate carcinoma, including androgen sensitive and insensitive prostate cancers, is also of interest. In some embodiments, patients are classified as metabolite producers and metabolite non-producers, where treatment may be tailored to the status of the patient. In certain embodiments, the ellagitannin metabolites of interest are urolithins.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

Any recited method can be carried out in the order of events recited or in any other order which is logically possible.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.); Molecular Probes (Eugene, Oreg.); Applied Biosystems, Inc. (Foster City, Calif.); and Glen Research (Sterling, Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modem Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds of the invention, or their pharmaceutically acceptable salts may contain one or more asymmetric centers and may thus give rise to enantiomers, diastereomers, and other stereoisomeric forms that may be defined, in terms of absolute /stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

Therepeutic uses of Ellagitannin Metabolites

Hyperproliferative disorders: refers to excess cell proliferation, relative to that occurring with the same type of cell in the general population and/or the same type of cell obtained from a patient at an earlier time. The term denotes malignant as well as non-malignant cell populations. Such disorders have an excess cell proliferation of one or more subsets of cells, which often appear to differ from the surrounding tissue both morphologically and genotypically. The excess cell proliferation can be determined by reference to the general population and/or by reference to a particular patient, e.g. at an earlier point in the patient's life. Hyperproliferative cell disorders can occur in different types of animals and in humans, and produce different physical manifestations depending upon the affected cells.

Hyperproliferative cell disorders include cancers; blood vessel proliferative disorders such as restenosis, atherosclerosis, in-stent stenosis, vascular graft restenosis, etc.; fibrotic disorders; psoriasis; inflammatory disorders, e.g. arthritis, etc.; glomerular nephritis; endometriosis; macular degenerative disorders; benign growth disorders such as prostate enlargement and lipomas; and autoimmune disorders. Cancers are of particular interest, including leukemias, lymphomas (Hodgkins and non-Hodgkins), and other myeloproliferative disorders; sarcomas, melanomas, adenomas, carcinomas of solid tissue, e.g. pancreatic cancer, colon cancer, prostate cancer, etc., hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, and the like.

Prostate cancer is now the most frequently diagnosed cancer in men. Prostate cancer is latent; many men carry prostate cancer cells without overt signs of disease. It is associated with a high morbidity. Cancer metastasis to bone (late stage) is common and is almost always fatal. Current treatments include radical prostatectomy, radiation therapy, hormonal ablation and chemotherapy. Unfortunately, in approximately 80% of cases, diagnosis of prostate cancer is established when the disease has already metastasized to the bones, thus limiting the effectiveness of surgical treatments. Hormonal therapy frequently fails with time with the development of hormone-resistant tumor cells. Although chemotherapeutic agents have been used in the treatment of prostate cancer, no single agent has demonstrated superiority over its counterparts, and no drug combination seems particularly effective. The generally drug-resistant, slow-growing nature of most prostate cancers makes them particularly unresponsive to standard chemotherapy.

As demonstrated in the Experimental section below, certain metabolites of ellagitannins (ET) have anti-proliferative and/or pro-apoptotic activities on cancer cells. Examples of such metabolites include urolithins A and B and derivatives thereof. As such, these metabolites or derivatives thereof find use in treating and/or preventing neoplastic diseases in subjects.

Although these metabolites are derived from ET present in certain foods (e.g., pomegranates), the consumption of these foods does not always lead to sufficient bioavailability of these therapeutic ET metabolites. Specifically, certain individuals, referred to herein as non-producers, fail to produce detectable amounts of these ET metabolites after consumption of ET-containing foods (e.g., pomegranate juice). Therefore, in certain embodiments, an ET metabolite(s) is administered directly to a subject having a neoplastic disease. In certain other embodiments, an ET metabolite(s) is administered directly to a subject to prevent the occurrence or recurrence of a neoplastic disease. In certain embodiments, the neoplastic disease is a cancer, including prostate cancer. In certain of these embodiments, the prostate cancer is androgen dependent or independent.

In certain embodiments, the ET metabolite or derivative thereof is an ellagic acid (EA) metabolite selected from the group consisting of urolithin B, urolithin A, methyl-urolithin A, hydroxyl-urolithin A and derivatives thereof. Also included in the methods of the invention are derivatives of urolithins, including pharmaceutically acceptable esters, etc., and derivatives having the structure:

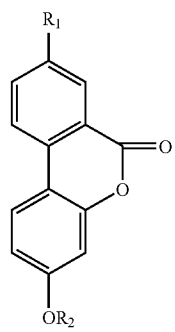

I where $R_1$ is H, OH, $OR_3$ where $R_3$ is a $C_1$ to $C_{10}$ lower alkyl, $NH_2$, $NHR_3$, SH, $SCH_3$, F, OCN, $O(CH_2)nNH_2$, $O(CH_2)nCH_3$ where n is from 1 to about 10; $C_1$ to $C_{10}$ lower alkyl, substituted lower alkyl, alkaryl or aralkyl; Cl, Br, CN, $CF_3$, $OCF_3$, O—, S—, or N-alkyl; O—, S—, or N-alkenyl; $SOCH_3$, $SO_2$; $CH_3$; $ONO_2$; $NO_2$; $N_3$; and $R_2$ is H, or $C_1$ to $C_{10}$ lower alkyl.

The ET metabolites or derivatives thereof may be administered to a subject (e.g., mammal) in a variety of ways. For example, the ET metabolite(s) can be administered orally, rectally, intravenously, intramuscularly, intraperitoneally, intra-cerobrospinally, subcutaneously, intra-articularly, intrasynovially, intrathecally, topically, or by inhalation. As such, the form of the ET metabolite dose can be in a variety of forms, including microcapsules, nano-capsules, liposomes, plasters, inhalation forms, nose sprays, sublingual tablets, and sustained-release preparations.

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional, additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like. Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres; slabs, etc. with biodegradable or non-biodegradable polymers. For example, polymers of lactic acid and/or glycolic acid form an erodible polymer that is well-tolerated by the host. The implant containing the inhibitory compounds may be placed in proximity to the site of a tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to, be achieved, and the pharmacodynamics associated with each compound in the host The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The combined use of the provided compounds of the present invention and other cytotoxic agents has the advantages that the required dosages for the individual drugs is lower, and the effect of the different drugs complementary. Depending on the patient and condition being treated and on the administration route, the subject compounds may be administered in dosages of at least about or around about 0.1 µg/kg body weight, at least about or around about 1 ng/kg body weight, at least about or around about 1 µg/kg body weight, at least about or around about 1 mg/kg body weight, at least about or around about 10 mg/kg body weight, per day or even higher values, and usually not more than about 100 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat maybe ten times the injection dose. Lower doses maybe used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the subject compounds may be formulated with other pharmaceutically active agents, particularly other anti-metastatic, antitumor or anti-angiogenic agents. Angiostatic compounds of interest include angiostatin, endostatin, carboxy terminal peptides of collagen alpha (XV), etc. Cytotoxic and cytostatic agents of interest include adriamycin, alkeran, Ara-C, BICNU, busulfan, CNNU, cis-platinum, cytoxan, daunorubicin, DTIC, 5-FU, hydrea, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

The urolithin compounds are useful for prophylactic or therapeutic purposes. As used herein, the term "treating" is used to refer to both prevention of disease, and treatment of pre-existing conditions. The prevention of proliferation is accomplished by administration of the subject compounds prior to development of overt disease, e.g., to prevent the regrowth of tumors, prevent metastatic growth, diminish restenosis associated with cardiovascular surgery, etc. Alternatively the compounds are used to treat ongoing disease, by stabilizing or improving the clinical symptoms of the patient.

The host, or patient, may be from any mammalian species, e.g., primate sp., particularly humans; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a. period of time sufficient to allow the active agents to induce cell death or inhibit migration, usually between about one hour and one week. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g., at least about 50%, decrease in the cell burden, and may be continued until there are essentially none of the undesirable cells detected in the body. The reduction is preferably at least about 10%, at least about 20%, at least about 30%, at least about 40%, at least about 50%, at least about 60%, at least about 70%, at least about 80%, at least about 90%, and ideally 100%.

As used herein, "prevention" of a condition (e.g., a neoplastic disease) means that the occurrence of the condition and/or its symptoms are reduced or eliminated. The reduction is preferably at least about 10%, at least about 20%, at least about 30%, at least about 40%, at least about 50%, at least about 60%, at least about 70%, at least about 80%, at least about 90%, and ideally 100%.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

EXPERIMENTAL

Example 1

Subjects, Materials and Methods

Reagents and Instruments. All solvents were HPLC grade and purchased from Fisher Scientific Co. (Tustin, Calif.). Ellagic, gallic, formic, phosphoric, 2-bromo-benzoic, 2-bromo-5-methoxybenzoic and acetic acids, resorcinol, potassium dihydrogen phosphate, ABTS (2,2□-aninobis-3ethylbenzothiazoline-6-sulphonic acid diammonium salt), manganese dioxide, Trolox (6-hydroxy-2,5,7,8-tetramethyl-chroman-2-carboxylic acid), magnesium chloride, Tris HCL, sodium acetate, diethylenetriamine pentaacetic acid (DTPA), deoxyguanosine (dG),β-D-glucuronidase (type X-A from *Escherichia coli*) and arylsulfatase (type VIII from abalone entrails) were purchased from Sigma-Aldrich (St. Louis, Mo.). The high performance liquid chromatography with ultraviolet detection (HPLC-UV) analyses were carried out on a Waters Alliance 2690 system equipped with a photo diode array (PDA) detector (Waters Corp., Milford, Mass.) and data handling was with Waters Millenium v 3.02 software. The high performance liquid chromatography with electrochemical detection (HPLC-ECD) system consisted of an Agilent Technologies 1100 quaternary pump, temperature regulated autosampler controlled by Chemstation Software 9.01 (Agilent Technology, Wilmington, Del.), an ESA 5600A coularrray electrochemical detector (ESA, Bedford, Mass.). The high performance liquid chromatography with mass spectroscopy (HPLC-MS) system consisted of an LCQ Classic Finnigan system (ThermoFinnigan, San Jose, Calif.), equipped with a HP 1100 series HPLC system consisting of an autosampler/injector, quaternary pump, column heater, and diode array detector (DAD) with Xcalibur 1.2 software (Finnigan Corp.).

HPLC-MS/MS analyses. Conditions for detection of ET-metabolites were as follows: Column, Symmetery C-18, 100 mm×2.1 i.d., 3.5 µm, (Waters Corp., Milford, Mass.); Solvent A) 2% HCOOH/H2O, B) 2% HCOOH/MeOH; gradient %A: initial: 99%, 30 min: 80%, 45 min: 60%, 60 min: 5%; run time 60 min; flow rate 0.15 mL/min; injection volume 20 µL; MS parameters: Ionization mode, electron spray ionization (ESI) in both positive and negative modes (see FIG. 3); scan range: 120-1500 amu; scan rate: 1 scan/sec; cone voltage: 17 eV. Peak identities were obtained by matching their molecular ions (M−H+) or (M+H+) obtained by ESI/MS and MS/MS with the expected theoretical molecular weights from literature data (4,5,13,15,18).

Cell culture materials. The 22Rv1, DU145, LNCaP and PC3 prostate cancer cell lines were obtained from American Type Culture Collection (ATCC, Rockville, Md.). The LNCaP-AR and Hi-Myc cell lines were a kind donation by Dr. C. Sawyers (David Geffen School of Medicine, UCLA, Los Angeles, Calif.). DU145, 22Rv1, LNCaP, LNCaP-AR, and PC3 cells were grown in RPMI 1640; Hi-Myc cells were grown in Isecove's Modified Dulbecco's Medium. All media contained 10% fetal bovine serum (FBS) in the presence of 100 U/mL penicillin and 0.1 g/L streptomycin. RWPE-1 prostate cells were grown in Defined Keratinocyte Serum Free Medium (DKSFM) containing epidermal growth factor (EGF), insulin and fibroblast growth factor (FGF). Cells were incubated at 37° C. with 95% air and 5% CO2. All cells were maintained below passage 20 and used in experiments during the linear phase of growth.

Syntheses of urolithin B and methyl-urolithin A. Urolithin (dibenzo[b,d]pyran-6-one) derivatives were synthesized according to the published method (21). Briefly, 2-bromobenzoic acid (5 g) and resorcinol (5 g) were suspended in aqueous NaOH solution (2 g/25 mL water), and refluxed for 30 min. After adding 5% aqueous $CUSO_4$ solution (15 mL), the mixture was refluxed for an additional 10 min. On cooling, urolithin B (3-hydroxy-6H-dibenzo[b,d]pyran-6-one) precipitated as a pale white powder and was re-crystallized from MeOH-glacial acetic acid (10:1) solution as needles. Similarly, 8-methoxyl-urolithin A (3-hydroxy-8-methoxyl-6H-dibenzo[b,d]pyran-6-one), was synthesized from 2-bromo-5-methoxybenzoic acid (1 g), resorcinol (1 g) and 8% aqueous NaOH solution (2 g/25 mL water; 10 mL). 8-methyl-urolithin A precipitated as a pale yellow powder from the solution and was re-crystallized from MeOH-glacial acetic acid solution (10:1) as needles. The LC-MSIMS data of the urolithin derivatives corresponded to published reports (5, 13-15).

Antiproliferative cell assay. Proliferation was measured utilizing the CellTiter-Glo® Luminescent Cell Viability Assay (Technical Bulletin #288, Promega Corp., Madison, Wis.). When added to cells, the assay reagent produces luminescence in the presence of ATP from viable cells. Cells were plated in 96-well plates at a density of 10,000 cells/well and incubated for 24 hours. Test samples were solubilized in DMSO by sonication, filter sterilized and diluted with media to the desired treatment concentration. Cells were treated with 100 µL control media, vehicle control (DMSO <0.2% of total) or test samples and incubated for 48 h drug exposure duration at 6.25, 12.5, 25, 50 and 100 µg/mL concentrations. At the end of 48 h, plates were equilibrated at room temperature for 30 min; 100 µL of the assay reagent was added to each well and cell-lysis was induced on an orbital shaker for 2 min. Plates were incubated at room temperature for 10 min to stabilize the luminescence signal and results were read on an Orion Microplate Luminometer (Bertholds Detection Systems, Pforzheim, Germany). All plates had control wells containing medium without cells to obtain a value for background luminescence. Data are expressed as percentage of untreated cells (i.e. treatment value-blank/vehicle value-blank), mean±SE for three replications.

Assessment of apoptosis. Apoptosis was assessed utilizing the Cell Death Detection ELISAPLUS Assay (Boehringer Mannheim, Indianapolis, Ind.). This assay is a photometric enzyme-linked immunoassay that quantitatively measures the internucleosomal degradation of DNA, which occurs during apoptosis. Specifically, the assay detects histone associated mono- and oligonucleosomes, which are indicators of apoptosis. Cells (22RV1, PC-3, LNCaP, LNCaP-AR), were plated in 60 mm dishes at a density of 100,000 cells/dish and allowed to attach for 24 hours. Cells were treated with vehicle control (100% DMSO; 0.3% final concentration), or urolithin B (0-50 µg/mL or 0-236 µM) for 48 hours. Following treatments, non-adherent cells were collected and pelleted at 200×g for ten minutes. The supernatant was discarded; the cell pellet was washed with cold CMF-PBS and re-centrifuged. Adherent cells were washed with cold calcium magnesium free- phosphate buffered saline (CMF-PBS, 137 mmol/L sodium chloride, 1.5 mmol/L potassium phosphate, 7.2 mmol/L sodium phosphate, 2.7 mmol/L potassium chloride, pH 7.4), trypsinized, collected and combined with non-adherent cells into a total of 1 mL DMEM. Both live and dead cells were then counted via trypan blue exclusion (Pierce, Rockford, Ill.) and equal numbers of cells were added to the microtiter plate for all treatment groups and apoptosis assay was performed according to the manufacturer's instructions. Data are expressed as absorbance at 405 nm of each sample over vehicle controls as follows=treatment value-blank/vehicle value-blank.

Results

Antiproliferative activity. EA and EA-metabolites (gallic and gallagic acids, urolithin B and methylated-urolithin A) were evaluated for antiproliferative activity against a panel of human prostate cancer cell lines (22Rv1, PC3, DU145, LNCaP, LNCaP-AR) and one mouse prostate cancer cell line (Hi-Myc). The IC50 values are shown in Table 1. The cell lines showed different levels of sensitivity towards specific metabolites as follows. Urolithin B was most effective against LNCaP-AR cells with an IC50 of 28.5 µM whereas the methylated derivative of urolithin A showed the greatest effect against this same cell line but at a much higher concentration with an IC50 of 150.7 µM. EA was most effective against the Hi-Myc cells with an IC-50 of 1.7 µM, gallic acid against 22Rv1 with IC50 of 18.6 µM and gallagic acid against LNCaP with an IC50 of 71.4 µM.

TABLE 1

IC50 values (μM) of EA and EA-metabolites against prostate cancer cell lines.

|  | Urolithin B | 8-methyl-Urolithin A | Ellagic acid | Gallic acid | Gallagic acid |
|---|---|---|---|---|---|
| 22 Rv1 | 117.6 | 127.0 | 41.7 | 18.5 | 166.1 |
| DU145 | 59.4 | 466.5 | 96.0 | 29.4 | 197.7 |
| HiMyc | 59.9 | 586.2 | 1.7 | 73.5 | 82.7 |
| LNCaP | 90.5 | 206.4 | 20.5 | 32.3 | 71.4 |
| LNCap-AR | 28.5 | 150.7 | 82.6 | 29.2 | 82.4 |
| PC3 | 127.2 | 526.4 | 83.6 | 110.9 | 83.6 |

Pro-Apoptotic Activity. Urolithin B was screened for ability to induce apoptosis of the 22Rv1, PC3, LNCaP and LNCaP-AR cell lines at concentrations ranging from 0 to 236 μM (0 to 50 μg/mL) as shown in FIGS. 5A-D. Urolithin B showed statistically significant pro-apoptotic effects against different cell lines as follows: 59 μM against 22Rv1 (p=0.05), 29.5 μM against PC3 (p=0.05), 118 μM against LNCaP (p=0.01) and 59 μM aganinst LNCaP-AR (p=0.01).

Discussion

The biological properties attributed to pomegranates and PJ has been related to its phenolic constituents and in particular to its major ET, punicalagin (3,6-9). We have previously investigated the anti-proliferative activity of a number of phenolic acids produced by the action of colonic bacteria on flavonoids from tea, soy and citrus and we found that activity was specific to a particular metabolite (32). In our current study we evaluated a number of potential and putative metabolites from pomegranate ETs, including ellagic, gallic and gallagic acids, urolithin B and methylated-urolithin A for antiproliferative activity against a panel of human prostate cancer cell lines (22Rv1, PC3, DU145, LNCaP, LNCaP-AR) and one mouse prostate cancer cell line (Hi-Myc) (Table 1). Although gallic acid has not been reported from bioavailability studies with pomegranate polyphenols, it may be present in a free state in pomegranates and/or released from the hydrolysis of gallotannins, known to be present in pomegranates. Gallic acid has one of the largest bioavailabilities among food phenolics (38). Due to the unavailability of a pure standard of urolithin A, it was not screened in the anti-cancer assays.

The characteristics of the cell lines are described as follows. The 22Rv1 is a human prostate carcinoma epithelial cell line with a weak response to androgen, expression of prostate serum antigen (PSA) and androgen receptor (AR). DU145 is a human metastatic prostate carcinoma isolated from the brain tissue, it does not respond to androgen, does not express PSA or the AR. PC3 is a bone metastasis from a patient with metastatic prostate carcinoma with a weak response to androgen, does not express PSA nor the AR. The LNCaP cell line is a human metastatic prostate carcinoma isolated from the lymph node. In contrast to the aforementioned three cell lines, the LNCaP cells are androgen responsive and express PSA and the AR. The LNCaP-AR cell line is the LNCaP cell line with the AR stably overexpressed. All five cell lines are tumorigenic in nude mice. The Hi-Myc is a murine cell line developed to overexpress the c-myc oncogene.

The pomegranate ET-metabolites significantly inhibited prostate cell proliferation in a dose dependent manner in cell lines tested ($p \leq 0.01$) and IC50 values are shown in Table 1. Our results provide data as to the ability of these compounds to inhibit the growth of different prostate cell lines.

In the antiproliferative assays, Urolithin B proved to be two to ten times more potent than methylated urolithin A in all cell lines tested, dependent upon the cell line. The cell lines were sensitive to urolithin B in the following order: LNCaP-AR<DU145<HiMyc<LNCaP<22Rv1<PC3 (Table 4). Gallic acid was up to nine times more effective at inhibiting the proliferation of prostate cancer cell lines than gallagic acid and up to three times as effective as ellagic acid (Table 1). The cell lines were sensitive to gallic acid in the following order: 22Rv1<LNCaP-AR<DU145<LNCaP<Hi-Myc<PC3. As with the metabolites, the most interesting result is that the LNCaP-AR cell line, which has an overexpressed androgen receptor (AR) is more sensitive to proliferative inhibition than the LNCaP parent cell line. Overexpression of the AR is a hallmark of androgen independent disease, therefore it is possible that the pomegranate metabolites may play a role in the prevention of the androgen independent stage of the disease.

Figure 5:
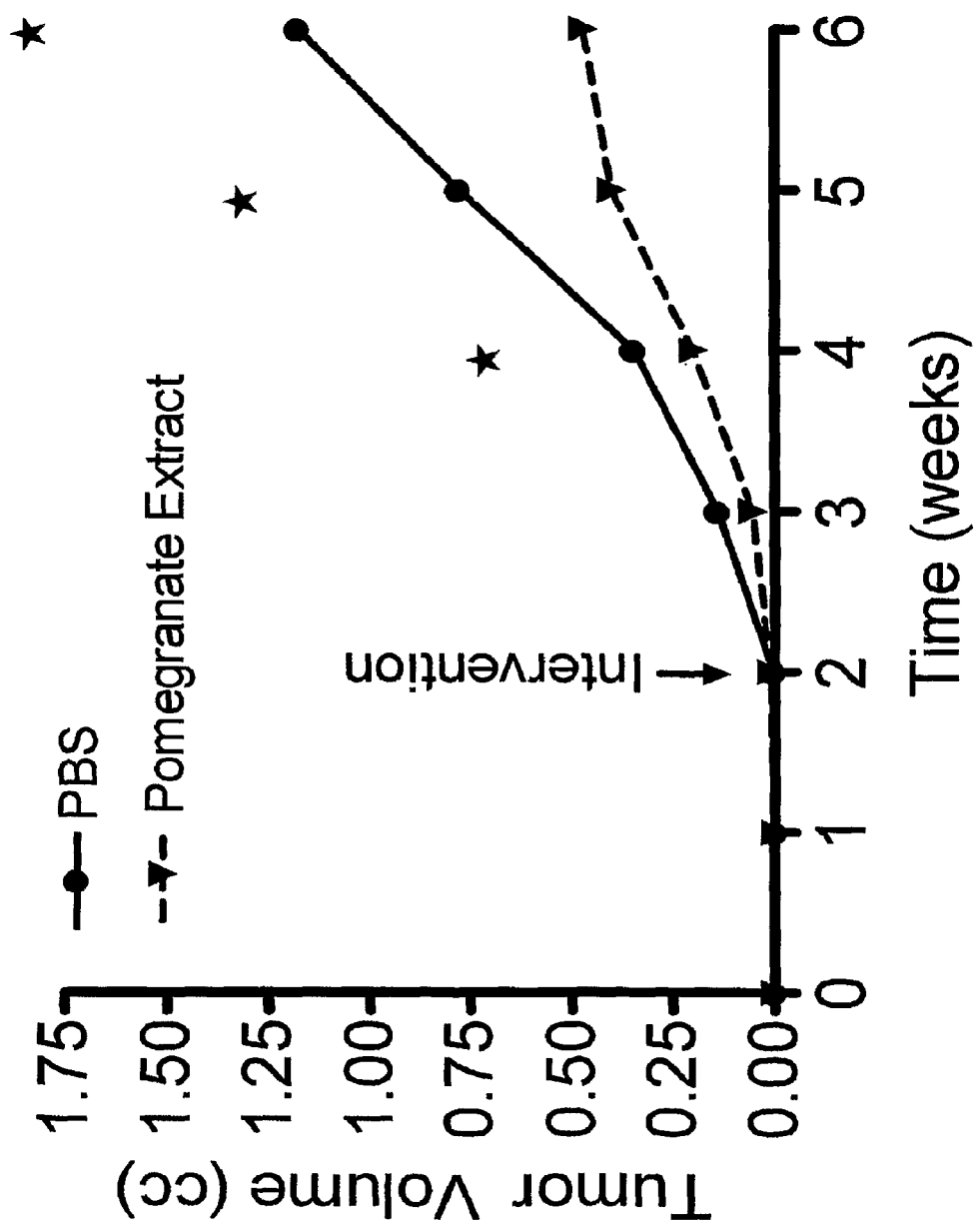
FIG. 5: Inhibition of tumor xenograft (LAPC-4) growth by PE in SCID mice. Inhibition of growth was significant beginning at two weeks after initiation of PE administration (0.8 mg/mouse/dose) orally (p<0.05) with greater than 50 percent inhibition of tumor volume by 6 weeks after tumor injection. PE or vehicle control was administered when tumors became palpable 2 weeks after injection of 200,000 prostate tumor cells (LAPC-4).

Whereas EA and other ETs have been shown to induce apoptosis in cancer cells, the pro-apoptotic effects of urolithins have not been reported. In our apoptosis studies, we screened urolithin B at concentrations ranging from 0 to 236 μM (O to 50 μg/mL) against PC3, 22Rv, LNCaP and LNCaP-AR cells (FIG. 5). The PC3, 22Rv1 and LNCaP-AR, cells were more sensitive towards urolithin B than the LNCaP cells (FIG. 5). Concentrations of urolithin B that induced apoptosis against these cells lines were 29.5, 59, 59 and 118 μM for PC3, 22Rv1m LNCaP-AR and LNCaP cells respectively. As with the proliferation data, the LNCaP-AR cell line was more sensitive to the effects of urolithin B than the LNCaP parent cell line suggesting that pomegranate consumption may play a role in the progression of prostate cancer.

A significant interindividual variability of urolithin production was noted among the study subjects leading to a potential classification into metabolite producers and non-producers. Similar interindividual variability has been observed for other polyphenols. The urolithins are produced as the result of metabolic transformations carried out by colonic microflora on EA and related compounds. Urolithins have been found in human urine collected 24 h after PJ ingestion and in rat urine, 4 days after pomegranate ET ingestion, suggesting that they are produced by colonic bacteria. EA and EA-metabolites (dimethyl ellagic acid-glucuronide, urolithin A-glucuronide and urolithin B-glucuronide) were detected in 24 h urine samples of fifteen of the nineteen subjects. Glucuronidation and methylation are part of the hepatic phase II metabolism which serves to increase water solubility and facilitate excretion. Metabolites that were the most prevalent in the subjects included dimethyl ellagic acid-glucuronide and urolithin B-glucuronide found in thirteen volunteers.

Potent antiproliferative activity against cancer cells has been demonstrated for many flavonoids but only a limited number of colonic metabolites have been tested. Urolithins have previously been evaluated for antioxidant and estrogenic activities. Our current study is the first to evaluate the antiproliferative activity of urolithins against a variety of human prostate cancer cell lines, 22Rv1, PC3, DU145, LNCaP (Table 1). EA exhibited the strongest antiproliferative activity in all cell lines (Table 1) with androgen-independent cells (DU145 and PC3) being more resistant. In the antiproliferative assays urolithin B proved to be two to ten times more potent than methyl urolithin A in all cell lines tested.

The pro-apoptotic effects of urolithins have also not been previously studied. In the apoptosis assay, the PC3 and 22Rv1 cells were more sensitive towards urolithin B than the LNCaP cells (FIGS. 4A-C).

In summary, we have identified ET metabolites that have anti-proliferative and pro-apoptotic activity towards cancer cells. As such, these metabolites find use as therapeutic agents for the treatment of neoplastic diseases. In addition, these findings make it possible to screen ellagitannin-containing compositions (e.g., food products) for their ability to produce these beneficial metabolites in an individual.

Example 2

Effect of Urolithins on Colon Cancer Cells

Antiproliferative activity. EA and EA-metabolites (gallic and gallagic acids, urolithin B and methylated-urolithin A) were evaluated for antiproliferative activity against the human colon cancer cell line HCT-116. The cells were grown to a concentration of 10,000 cells per well in a 96 well format; and were then resuspended in medium containing vehicle control or the indicated compound: Ellagic acid, urolithin A, methyl urolithin A, or urolithin B, at a concentration of 100 µg/mL. The cells were incubated for 48 hrs, and the viability assayed by the CellTiter-Glo® Luminescent Cell Viability Assay (Technical Bulletin #288, Promega Corp., Madison, Wis.).

Figure 3:
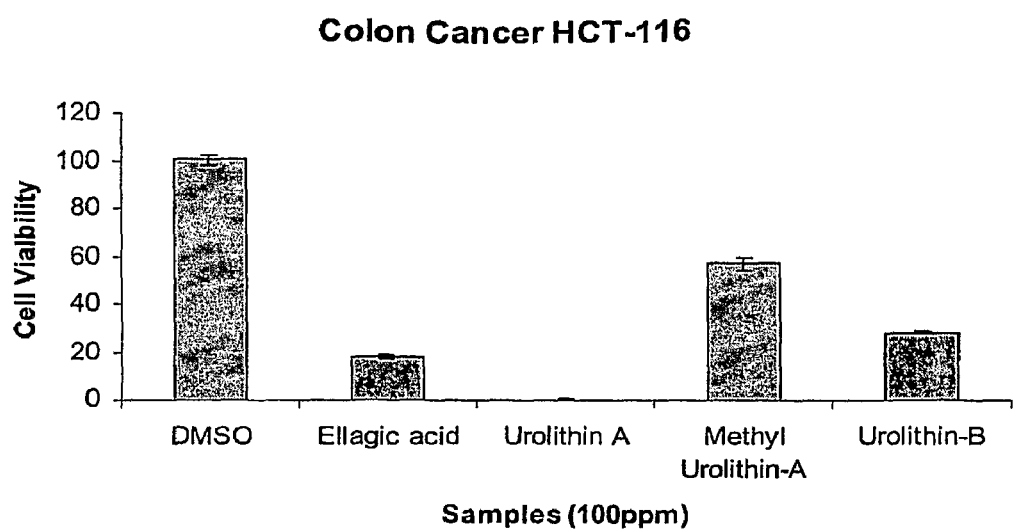
FIG. 3: Anti-proliferative activity of urolithins against a human colon cancer cell line HCT-116.

These data, as shown in FIG. 3, demonstrate the efficacy of the ellagitannin metabolites as anti-proliferative agents. The data show that urolithin A is the most active, then ellagic acid, urolithin B and methyl urolithin A.

Example 3

Effect of Urolithins on Pancreatic Cancer Cells

Antiproliferative activity. EA and EA-metabolites (gallic and gallagic acids, urolithin B and methylated-urolithin A) were evaluated for antiproliferative activity against the human pancreatic cancer cell lines ASPC-1 and BXPC-3. The cells were grown to a concentration of 10,000 cells per well; and were then resuspended in medium containing the vehicle control or the indicated compound: Ellagic acid, urolithin A, methyl urolithin A, or urolithin B, at a concentration of 100 µg/mL. The cells were incubated for 48 hrs, and the viability assayed byCeliTiter-Glo® Luminescent Cell Viability Assay (Technical Bulletin #288, Promega Corp., Madison, Wis.).

Figure 4:
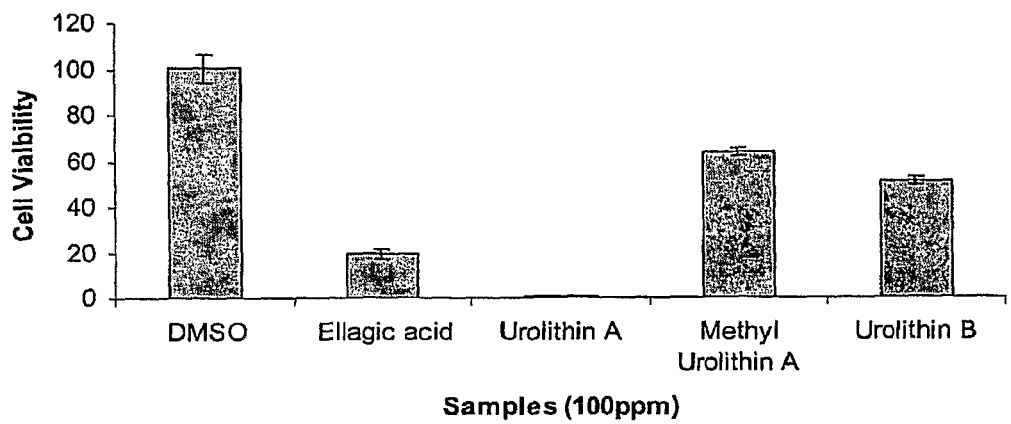
FIGS. 4A and 4B. Anti-proliferative activity of urolithins against human pancreatic cell lines ASPC-1 and BXPC-3.
Figure 4:
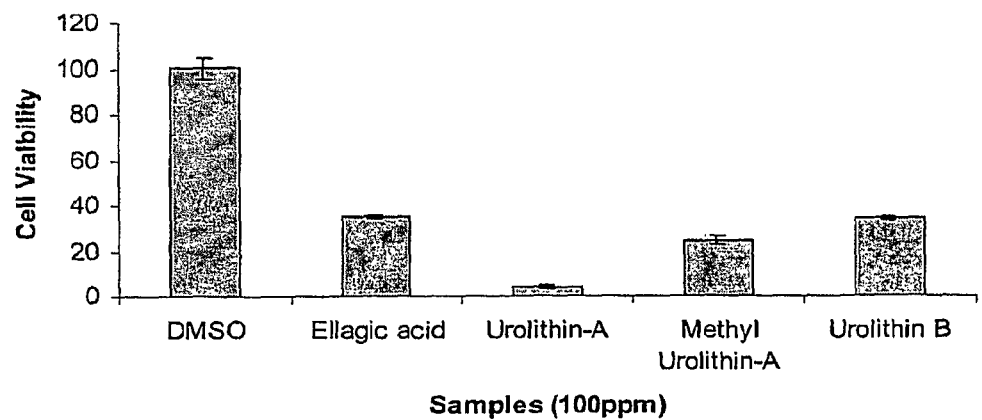

These data shown in FIG. 4 demonstrate the efficacy of the ellagitannin metabolites as anti-proliferative agents. The data show that urolithin A is the most active, then ellagic acid, urolithin B and methyl urolithin A.

Example 4

Pomegranate Ellagitannin Derived Metabolites Inhibit Prostate Cancer Growth and Localize to the Mouse Prostate Gland Pomegranate juice has previously been shown in a Phase II clinical trial to increase prostate specific antigen (PSA) doubling time in prostate cancer (CaP) patients with a rising PSA. Using a standardized pomegranate extract (PE), we sought to further define the metabolism and tissue distribution of pomegranate metabolites, and its effects in vivo on human CaP xenograft growth in a well-established pre-clinical model.

PE and a pomegranate metabolite, urolithin A (UA), were administered to male mice and metabolite levels in plasma and tissues were determined over twenty-four hours. PE or vehicle control was administered orally to severe combined immunodeficient (SCID) mice injected subcutaneously with human CaP cells (LAPC-4). The in vitro effects of the pomegranate metabolites, ellagic acid (EA) and urolithins were studied in androgen-dependent and independent CaP cell lines.

Pomegranate metabolites were concentrated at higher levels in mouse prostate and intestinal tissues compared to other tissues after administration of PE or UA. PE significantly inhibited LAPC-4 xenograft growth in SCID mice. PE metabolites, EA and urolithins, inhibited androgen-dependent and independent CaP cell growth in vitro.

Anticancer effects of PE in pre-clinical models of CaP and localization of bioactive metabolites in prostate tissue demonstrate that PE can play a role in CaP treatment and chemoprevention. These results form a sound basis for clinical trials in men with CaP.

Pomegranate juice consumption by prostate cancer (CaP) patients with rising prostate specific antigen (PSA) following primary therapy, significantly increased the mean PSA doubling time from 15 to 54 months (p<0.001). Ellagitannins (ETs) are the predominant polyphenols found in pomegranate fruits, and are also the most abundant polyphenols in some berry fruits such as strawberries, red raspberries, black raspberries and muscadine grapes. Published studies have shown that ETs and their hydrolysis product, ellagic acid (EA), inhibit CaP cell growth through cell-cycle arrest and stimulation of apoptosis. Pomegranate juice and pomegranate extracts (PEs) have also been shown to inhibit CaP growth in vitro (see Seeram et al. *J Nutr Biochem.* 16 (2005), p. 360; Lansky et al. *Invest New Drugs* 23 (2005), p. 11). Likewise, PEs administered in animal diets have been shown to inhibit CaP xenograft growth in severe-combined immunodeficient (SCID) mice (see Albrecht et al. *Med Food* 7 (2004), p. 274; Malik et al. *Proc Natl Acad Sci. USA* 102 (2005), p. 14813).

In human volunteers, pomegranate juice ETs are hydrolyzed to EA, and then further converted by gut bacteria to yield bioavailable 'Urolithin A (UA)' derivatives (see Seeram et al. *J Nutr Biochem.* 16 (2005), p. 360; Lansky et al. *Invest New Drugs* 23 (2005), p. 11; Albrecht et al. *Med Food* 7 (2004), p. 274; Malik et al. *Proc Natl Acad Sci. USA* 102 (2005), p. 14813; Seeram et al. *J Nutr.* 136 (2006), p. 2481; Cerda et al. *Eur J Nutr.* 43 (2004), p. 205; Cerdá, et al. *J Agric Food Chem.* 53 (2005), p. 227; Cerda et al. *Eur J Clin Nutr.* 60 (2006), p. 245). Urolithins appear in blood, urine and feces of human volunteers 12-24 h after consumption of a single dose of ET-rich beverages or foods and persist in vivo for up to 48-56 h after ingestion. Despite these advances in understanding pomegranate ET metabolism in rodents, and humans, there have been no studies determining the disposition of ET metabolites to tissues of interest including the prostate, and no in vitro studies evaluating antiproliferative effects of urolithins. Therefore, we planned the current studies to explore the bioactivity and tissue distribution of PE and UA, the effects of orally administered PE on CaP xenograft growth in SCID mice, and effects of EA and UA derivatives on human androgen dependent (LNCaP) and independent CaP cell lines in vitro.

Materials and Methods

Pomegranate Extract. Pomegranate extract (PE) derived from the skin of pomegranate fruit (*Punica granatum* L., Paramount Farms, Lost Hills, Calif.) was standardized to 37% ETs (as punicalagins) and 3.5% free EA as reported (Seeram et al. *Sep Purific Tech.* 41 (2005), p. 49). PE was administered to animals in doses based on the amount of ETs in a single serving of pomegranate juice (240 ml of single strength juice, 80 mg of ETs). The equivalent dose that would be administered to a 70 kg human was calculated for a mouse of 25 g body weight to be 0.03 mg ETs. Ten times (10×) this dose was used in the animal studies (0.8 mg PE per dose per animal) to enhance our ability to detect phytochemical distribution. For studies administering UA, doses were calculated assuming complete conversion of ETs to UA. This results in a dose of 0.3 mg of purified synthesized UA per animal. Both PE and UA were suspended in 50 μL PBS or 10% aqueous glucose solution for intraperitoneal or oral administration, respectively.

Tissue Disposition Studies. Male C57/B6 mice (n=156 mice, retired breeders, 7 months old, 25-30 g) from Charles River laboratories (Wilmington, Mass.) were fed AIN 93G diets and water ad libitum, and fasted 6 h prior to dosing. Mice were dosed orally or intraperitoneally with either PE (0.8 mg/mouse/dose; n=72), UA (0.3 mg/mouse/dose; n=72) or vehicle control (50 μL; n=12 mice). Blood samples were collected at 0.5, 1, 2, 4, 6 and 24 h after dosing and prostate, liver, kidney, lung, colon, intestine and brain tissues were collected and stored at −80° C. Harvested tissue (200 mg) was homogenized in methanol with 0.1% acetic acid (1 mL) and centrifuged at 3000×g for 10 min. The supernatant was dried on a SpeedVac then reconstituted with 200 μL of the HPLC mobile phase for a final injection volume of 20 μL. Xenograft tissue homogenates required acid hydrolysis prior to chromatography as reported (Gu et al. *J Agric Food Chem.* 53 (2005), p. 6858). HPLC-UV and HPLC-MS/MS analyses were carried out on a Waters Alliance 2690 system (Waters Corp., Milford, Mass.) an LCQ Classic Finnigan system (ThermoFinnigan, San Jose, Calif.), respectively, as previously described (Seeram et al. *Clin Chim Acta.* 348 (2004), p. 63). Linear calibration curves were constructed using a spiked internal standard method with EA or UA using plasma or liver tissues collected from control mice as described previously (Seeram et al. *Clin Chim Acta.* 348 (2004), p. 63). Accuracy values ranged from 91-108% for the quality control samples containing the EA or UA standard.

Xenograft Study. All mice received a standard research diet (AIN 93G, Dyets, Bethlehem, Pa.) ad lib throughout the experiment. $2\times10^6$ androgen-dependent LAPC-4 prostate cancer cells (gift from Charles Sawyers) were implanted subcutaneously into the shoulders of twenty-four 5 week-old SCID mice (Taconic Farm, Germantown, N.Y.). When tumors became palpable mice were administered either PE (n=12 mice) or vehicle control (n=12 mice) orally 5 days per week (Monday-Friday). Oral dosing was accomplished by gently securing the mouse with one hand and delivering the PE or vehicle control via an animal feeding needle (Biomedical Needles, Popper and Sons Inc., New Hyde Park, N.Y.) attached to a 1 mL tuberculin syringe. Tumors were measured twice weekly and mice were weighed weekly. Tumor volumes were calculated using the formula: length×width×height×0.5236 (Gleave et al. *Cancer Res.* 51 (1991); p. 3753). At sacrifice, primary tumors were excised and blood collected. All animal protocols were approved by University of California, Los Angeles Chancellor's Animal Care Committee.

In Vitro Proliferation Studies. DU145 and LNCaP cells (ATCC, Rockville, Md.), 22Rv1 cells (gift from Pinchas Cohen), and LNCAP-AR cells (gift from Charles Sawyers) were maintained below passage 20 and used in experiments during the linear phase of growth as previously described (Seeram et al. *J Nutr Biochem.* 16 (2005), p. 360). EA was purchased from Sigma-Aldrich (St. Louis, Mo.). UA (3,8-dihydroxy-6H-benzo[b,d]chromen-6-one), methylated UA and dimethylated UA were synthesized in our laboratory as previously described (Ghosal et al. *J Chem Res Synop.* 11 (1989), p. 350). Compounds were dissolved in dimehylsulfoxide (DMSO) then added to media to achieve the final desired test concentration with a final DMSO concentration not exceeding 0.1%. Proliferation was determined by tritiated thymidine uptake as previously described. All assays were performed in triplicate.

Statistical Analysis. For the cell proliferation assays, data are expressed as a percentage of untreated cells (i.e. treatment value-blank/vehicle value-blank), mean±SE for at least three separate experiments. Data were analyzed by either student's t-test or one-way ANOVA followed by Dunnett's Multiple Range test ($\alpha$=0.05) with Graph Pad Prism 3.0 (Graph Pad Software Inc.) as appropriate. The statistical package R.2.5.1 was used to compute descriptive statistics and generate the plots displayed in FIG. 6.

Results

Inhibition of Xenograft Growth. Oral PE administration led to a significant inhibition of LAPC-4 xenograft growth relative to the vehicle control group (FIG. 5). Tumor volumes were significantly reduced in the PE-treated group relative to the control group at four weeks (0.35±0.19 vs. 0.20±0.14 cm$^3$; p=0.0280), five weeks (0.78±0.39 vs. 0.39±0.26 vs. cm$^3$; p=0.005) and six weeks (1.18+0.37 vs. 0.47+0.28 cm$^3$; p=0.0002) after tumor cell injectio EA was found at higher concentrations in tumor tissues collected from three PE treated mice (1030±124.9 ng/g) compared to mice receiving vehicle-control (316.3±54.1 ng/g; p=0.0008). UA and its metabolites were not detected in xenograft tissues.

Tissue Distribution of Pomegranate Extract Metabolites. After oral administration of PE (to mice without xenografts), EA was detected in plasma at 0.5 h and was cleared after 2 h. Intraperitoneally administered PE gave higher plasma EA levels at 0.5 h as compared to oral dosing (134.5±12 vs. 11.5±1.4 ng/mL) and persisted in plasma for 6 h. EA was not detected in prostate tissue after oral PE administration, whereas it was detected at high concentrations in prostate tissue (676±172 ng/g) and to a lesser extent in intestine, colon, and liver after intraperitoneal administration. UA, a metabolite of EA, was not detected in plasma or tissues following PE administration.

Figure 6A:
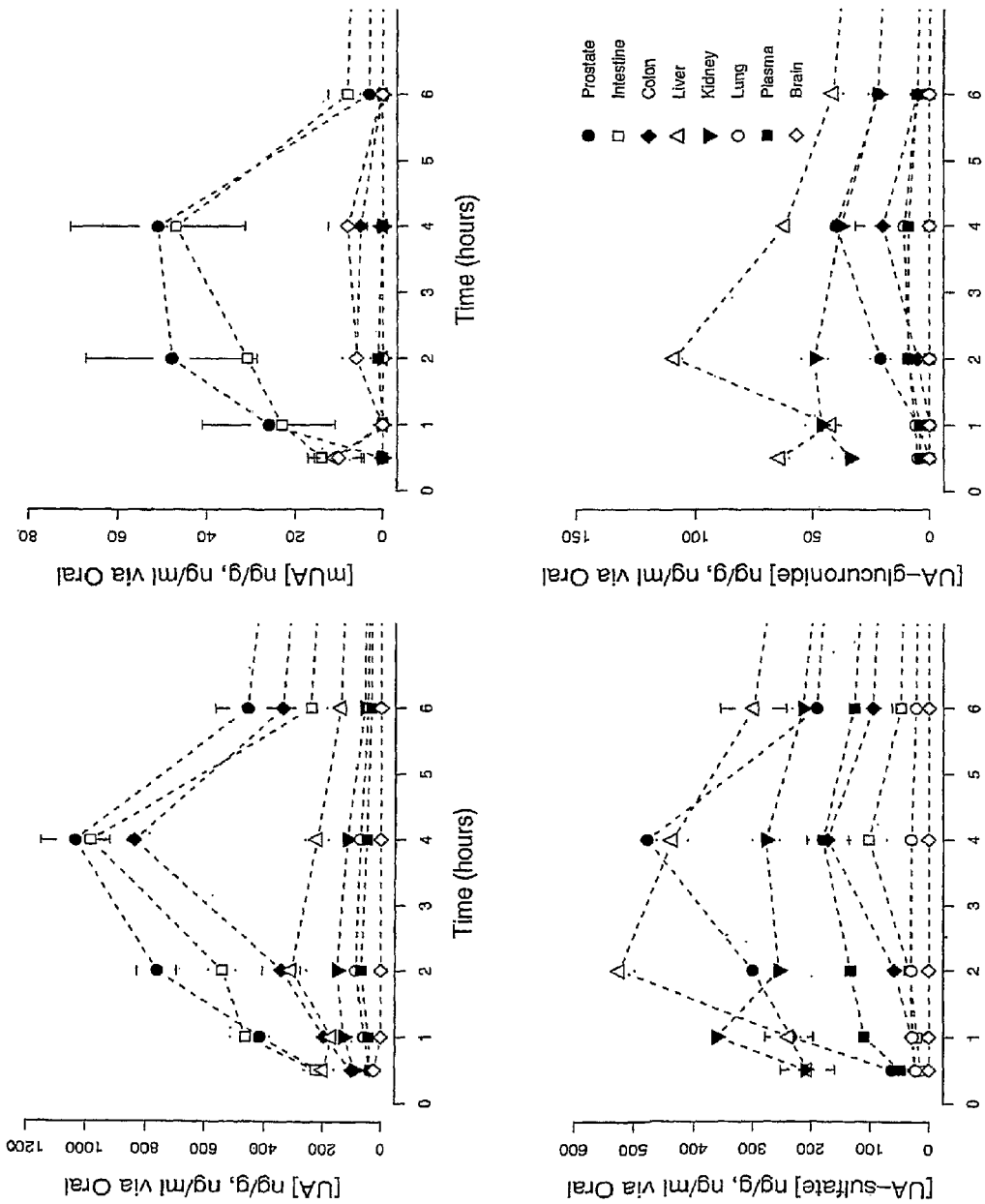
FIGS. 6A-6B. (A) Concentrations of urolithin A (UA) and UA-conjugates: methylated UA, UA sulfate, and UA -glucuronide in plasma (ng/mL) and tissues (ng/g) of mice that received UA (0.3 mg/mouse/dose) by the oral route. Metabolite levels at the 24 h time point were below the detectable limit (3 ng/mL for blood and 5 ng/g for tissues) and are therefore not shown. Data show the mean±SE for n=6 mice per time point. (B) Concentrations of urolithin A (UA) and UA-conjugates: methylated UA, UA sulfate, and UA-glucuronide in plasma (ng/mL) and tissues (ng/g) of mice that received UA (0.3 mg/mouse/dose) by the intraperitoneal route. Metabolite levels at the 24 h time point were below the detectable limit (3 ng/mL for blood and 5 ng/g for tissues) and are therefore not shown. Data show the mean±SE for n=6 mice per time point.
Figure 6B:
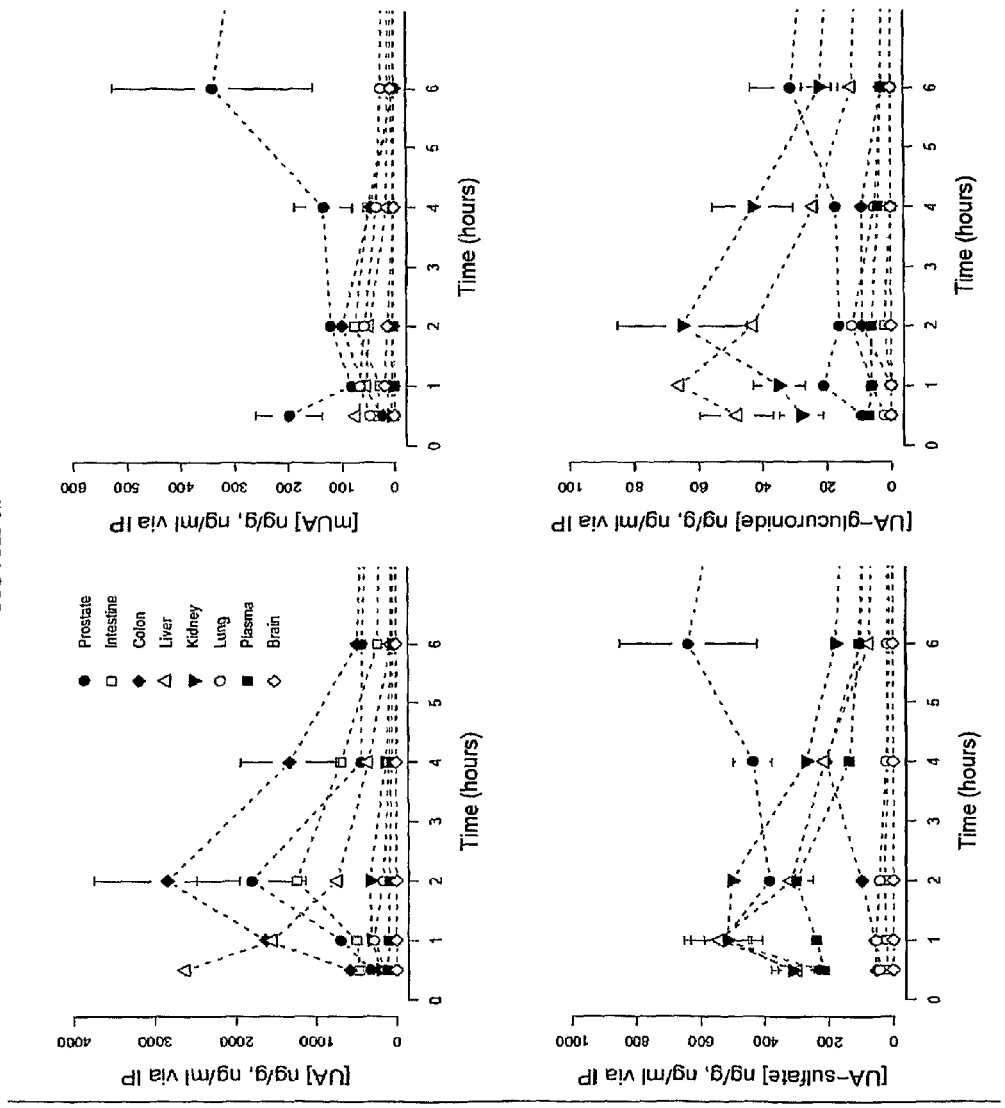

Orally administered UA was rapidly absorbed and taken up in highest concentrations in the prostate gland followed by the small intestine and colon (FIG. 6A). Intraperitoneally administered UA concentrated in the prostate, colon, and intestine with a peak at 2 hr (FIG. 6B). Among the UA metabolites, UA-sulfate and methylated UA were detected primarily in the prostate gland whereas UA-glucuronide was found in greatest concentration in liver and kidney tissues.

Bioactivity of PE Metabolites in vitro. EA, synthesized UA and synthesized UA metabolites were incubated at 10-100 μmol/L concentrations with androgen-dependent (LNCaP) and independent CaP cell lines (LNCaP-AR, DU145, and 22RV1). All metabolites demonstrated dose dependent antiproliferative effects on all cell lines tested. The IC$_{50}$ of UA was lower than that for EA in all cell lines (Table 2). Among the UA metabolites, methylated UA had the greatest bioactivity in inhibiting LNCaP and 22RV1 cell growth. The IC50 values for each metabolite are summarized in Table 2.

TABLE 2

IC$_{50}$ (μmol/L) values of pomegranate ellagitannin metabolites on growth of human prostate cancer cells.

| Cells | EA | UA | mUA | dmUA |
|---|---|---|---|---|
| LNCaP | 62.4 ± 4.2 | 31.3 ± 0.5 | 15.9 ± 4.7 | 71.4 ± 13.5 |
| LNCaP-AR | 78.7 ± 3.2 | 43.3 ± 2.8 | 126.7 ± 7.3 | ND |

TABLE 2-continued

IC$_{50}$ (μmol/L) values of pomegranate ellagitannin metabolites on growth of human prostate cancer cells.

| Cells | EA | UA | mUA | dmUA |
|---|---|---|---|---|
| DU145 | 74.3 ± 5.2 | 49.8 ± 3.9 | 43.3 ± 3.5 | 70.7 ± 13.0 |
| 22RV1 | 108.7 ± 16.6 | 47.8 ± 3.2 | 6.2 ± 0.8 | 85.0 ± 8.6 |

Data are expressed as percentage of untreated cells (i.e. treatment value-blank/vehicle value-blank), mean ± SE for at least three separate experiments.
[1]UA = UA, mUA = methylated UA; dmUA = dimethylated UA.

The present studies were designed to determine the tissue disposition of pomegranate extract metabolites, EA and urolithins, and to determine if the metabolites localize in the prostate gland and prostate tumor xenografts. Urolithin A (UA) was studied in detail. In the present study, oral administration of PE to mice led to increased plasma levels of EA, but EA were not detected in the prostate gland. On the other hand, intraperitoneal administration of PE led to tenfold higher EA levels in the plasma, and detectable and higher EA levels in the prostate, intestine, and colon relative to other organ systems. The detectable EA levels in prostate tissue following intraperitoneal but not oral administration was likely due to higher plasma levels attained after intraperitoneal administration. Intraperitoneal and oral administration of UA led to uptake of UA and it conjugates in prostate tissue, and the urolithin levels were higher in prostate and intestinal tissues relative to other organ system. Importantly, the predilection of bioactive pomegranate metabolites to localize in prostate tissue combined with pre-clinical data demonstrating anticancer effects demonstrates the potential for pomegranate products to play a role in chemoprevention of prostate cancer.

This is the first study demonstrating that urolithins have potent antiproliferative activity against androgendependent and androgen-independent prostate cancer cell lines, with IC50 values lower than EA.

Following administration of UA, a number of UA-conjugates were detectable in the prostate gland. UA and other polyphenols are metabolized by hepatic phase-II enzymes including glucuronosyl transferases to form glucuronides, sulfotransferases to form sulfates, and catechol-o-methyl transferases to from methylated derivatives. These phase-II metabolic processes increase the hydrophilicity of the metabolites and facilitate their excretion. UA-sulfate was the major metabolic product of UA in this study suggesting that among phase-II enzymes, the sulfotransferases played the major role in UA transformation. Of importance, UA and UA-conjugates that concentrated in the mouse prostate in the present study had antiproliferative activity against human androgen sensitive and insensitive CaP cell lines.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method of treating a solid tumor in a human, said method comprising:
    administering to a human in need thereof an effective amount of a urolithin selected from the group consisting of urolithin B, urolithin A, and methyl-urolithin A, wherein the solid tumor is selected from prostate cancer, pancreatic cancer and colon cancer.
2. The method of claim 1, wherein said solid tumor is prostate cancer.
3. The method of claim 1, wherein said solid tumor is pancreatic cancer.
4. The method of claim 1, wherein said solid tumor is colon cancer.
5. The method of claim 1, wherein said urolithin is urolithin B.
6. The method of claim 1, wherein said urolithin is urolithin A.
7. The method of claim 1, wherein said urolithin is methyl-urolithin A.
8. The method of claim 1, wherein said solid tumor is prostate cancer; and said urolithin is urolithin B.
9. The method of claim 1, wherein said solid tumor is pancreatic cancer; and said urolithin is urolithin B.
10. The method of claim 1, wherein said solid tumor is colon cancer; and said urolithin is urolithin B.
11. The method of claim 1, wherein said solid tumor is prostate cancer; and said urolithin is urolithin A.
12. The method of claim 1, wherein said solid tumor is pancreatic cancer; and said urolithin is urolithin A.
13. The method of claim 1, wherein said solid tumor is colon cancer; and said urolithin is urolithin A.
14. The method of claim 1, wherein said solid tumor is prostate cancer; and said urolithin is methyl-urolithin A.
15. The method of claim 1, wherein said solid tumor is pancreatic cancer; and said urolithin is methyl-urolithin A.
16. The method of claim 1, wherein said solid tumor is colon cancer; and said urolithin is methyl-urolithin A.

* * * * *